(12) United States Patent
Fruehsorger et al.

(10) Patent No.: US 9,764,623 B2
(45) Date of Patent: Sep. 19, 2017

(54) VEHICLE AIR CONDITIONER DEVICE

(71) Applicant: AUDI AG, Ingolstadt (DE)

(72) Inventors: Alexander Fruehsorger, Beijing (CN); Xuefeng Wang, Beijing (CN)

(73) Assignee: AUDI AG, Ingolstadt (DE)

( * ) Notice: Subject to any disclaimer, the term of this patent is extended or adjusted under 35 U.S.C. 154(b) by 49 days.

(21) Appl. No.: 14/651,776

(22) PCT Filed: Dec. 12, 2012

(86) PCT No.: PCT/CN2012/086461
§ 371 (c)(1),
(2) Date: Jun. 12, 2015

(87) PCT Pub. No.: WO2014/089785
PCT Pub. Date: Jun. 19, 2014

(65) Prior Publication Data
US 2015/0360544 A1 Dec. 17, 2015

(51) Int. Cl.
*B60H 3/06* (2006.01)
*B60H 1/24* (2006.01)
(Continued)

(52) U.S. Cl.
CPC ........... *B60H 3/0078* (2013.01); *A61L 9/22* (2013.01); *B03C 3/017* (2013.01); *B60H 1/008* (2013.01); *B60H 1/00821* (2013.01); *B60H 1/00985* (2013.01); *B60H 3/0085* (2013.01); *B60H 3/06* (2013.01); *B60K 35/00* (2013.01); *F24F 3/16* (2013.01); *F24F 11/0001* (2013.01);
(Continued)

(58) Field of Classification Search
CPC .......... B60H 3/06; B60H 1/24; B60H 3/0085; B60H 3/0625; B60H 3/0092; F24F 11/00
USPC .......... 55/385.3, 312, DIG. 34; 454/75, 139, 454/158
See application file for complete search history.

(56) References Cited

U.S. PATENT DOCUMENTS 5,954,577 A * 9/1999 Meckler ............... B60H 3/0625
454/158
6,375,714 B1 4/2002 Rump et al.
(Continued)

FOREIGN PATENT DOCUMENTS

CN 1562653 1/2005
CN 101015727 8/2007
(Continued)

OTHER PUBLICATIONS

International Search Report for PCT/CN2012/086461, mailed Sep. 19, 2013, 6 pages.
Written Opinion on the International Searching Authority for PCT/CN2012/086461, mailed Sep. 19, 2013, 5 pages.

*Primary Examiner* — Jacob T Minskey
*Assistant Examiner* — Minh-Chau Pham
(74) *Attorney, Agent, or Firm* — Staas & Halsey LLP

(57) ABSTRACT

The present invention relates to a vehicle air conditioner device, comprising: an air purifying unit for regulating air quality inside the vehicle; an inside air quality acquiring unit for acquiring air quality inside the vehicle; an outside air quality acquiring unit for acquiring air quality outside the vehicle; and a display unit for displaying information related to the acquired air quality inside the vehicle and information related to the acquired air quality outside the vehicle.

12 Claims, 4 Drawing Sheets

(51) Int. Cl.
　　*F24F 11/00*　　(2006.01)
　　*B60H 3/00*　　(2006.01)
　　*F24F 3/16*　　(2006.01)
　　*B60H 1/00*　　(2006.01)
　　*A61L 9/22*　　(2006.01)
　　*B03C 3/017*　　(2006.01)
　　*B60K 35/00*　　(2006.01)

(52) U.S. Cl.
　　CPC ............... *F24F 2011/002* (2013.01); *F24F 2011/0091* (2013.01); *Y02B 30/78* (2013.01)

(56) References Cited

U.S. PATENT DOCUMENTS

| | | | |
|---|---|---|---|
| 7,462,214 B2 * | 12/2008 | Sassa | B60H 1/00842 454/75 |
| 2008/0078289 A1 * | 4/2008 | Sergi | B01D 46/0013 95/25 |
| 2009/0312905 A1 | 12/2009 | Marra | |
| 2010/0144261 A1 | 6/2010 | Barkic et al. | |

FOREIGN PATENT DOCUMENTS

| | | |
|---|---|---|
| CN | 101256019 | 9/2008 |
| CN | 101718770 | 6/2010 |
| CN | 202141710 | 2/2012 |
| CN | 102529647 | 7/2012 |
| CN | 102806825 | 12/2012 |
| CN | 102837580 | 12/2012 |
| EP | 2075512 | 7/2009 |
| JP | 61-9323 | 1/1986 |
| JP | 4-284811 | 10/1992 |
| JP | 8-238921 | 9/1996 |
| JP | 9-309328 | 12/1997 |
| JP | 9-309331 | 12/1997 |
| JP | 10-329537 | 12/1998 |
| JP | 2004-168074 | 6/2004 |
| JP | 2005-145340 | 6/2005 |
| JP | 2006-111182 | 4/2006 |
| JP | 2010-25562 | 2/2010 |
| WO | 2004/014442 | 2/2004 |
| WO | PCT/CN2012/086461 | 12/2012 |

* cited by examiner

VEHICLE AIR CONDITIONER DEVICE

CROSS REFERENCE TO RELATED APPLICATIONS

This application is based on and hereby claims priority to International Application No. PCT/CN2012/086461 filed on Dec. 12, 2012, the contents of which are hereby incorporated by reference.

BACKGROUND OF THE INVENTION

Field of the Invention

The present invention relates to an air conditioner device, and in particular to an air conditioner device for a vehicle.

Description of the Related Art

The control of a vehicle air conditioner normally includes temperature control, humidity control, air volume and air direction control, switching control of internal and external circulation modes and so on. As the popularity of vehicles gradually increases, people tend to spend more time in the vehicle and begin to pay more attention to the air quality inside the vehicle. Especially in those areas with severe air pollution, in order to guarantee the air quality inside the vehicle, the air conditioner device also comprises a filter with activated carbon, ionizer or the like, so as to prominently improve the air quality inside the vehicle.

However, a user can only subjectively sense whether the air quality inside the vehicle is improved but cannot acquire a visual air quality evaluation. If the user can be provided with a visual display of the air quality inside and outside the vehicle, the advantage of meeting the user's psychological needs will become obvious.

SUMMARY OF THE INVENTION

As for the problem in the prior art that the user cannot obtain the air quality inside and outside the vehicle, the present invention provides a vehicle air conditioner device capable of simultaneously displaying air quality inside and outside the vehicle.

In order to solve the above-mentioned technical problem, there is provided a vehicle air conditioner device according to the embodiments of the present invention, comprising: an air purifying unit for regulating air quality inside the vehicle; an inside air quality acquiring unit for acquiring air quality inside the vehicle; an outside air quality acquiring unit for acquiring air quality outside the vehicle; and a display unit for displaying information related to the acquired air quality inside the vehicle and information related to the acquired air quality outside the vehicle.

By simultaneously displaying air quality information inside and outside the vehicle, the vehicle air conditioner device according to the embodiments of the present invention can let the user have intuitive feelings. Moreover, according to the above-mentioned information displayed by the display unit, the user can switch between the internal and external circulation modes, and start up or shut off the ionizer, in-vehicle climate control unit, air purifying unit and so on via a human-machine interface (HMI), which further benefit the improvement of the air quality inside the vehicle and can satisfy the user's actual needs and personal will for the air quality inside the vehicle.

DETAILED DESCRIPTION OF THE PREFERRED EMBODIMENTS

The vehicle air conditioner device according to the embodiments of the present invention will now be described in detail below with reference to the drawings.

First Embodiment

Figure 1:
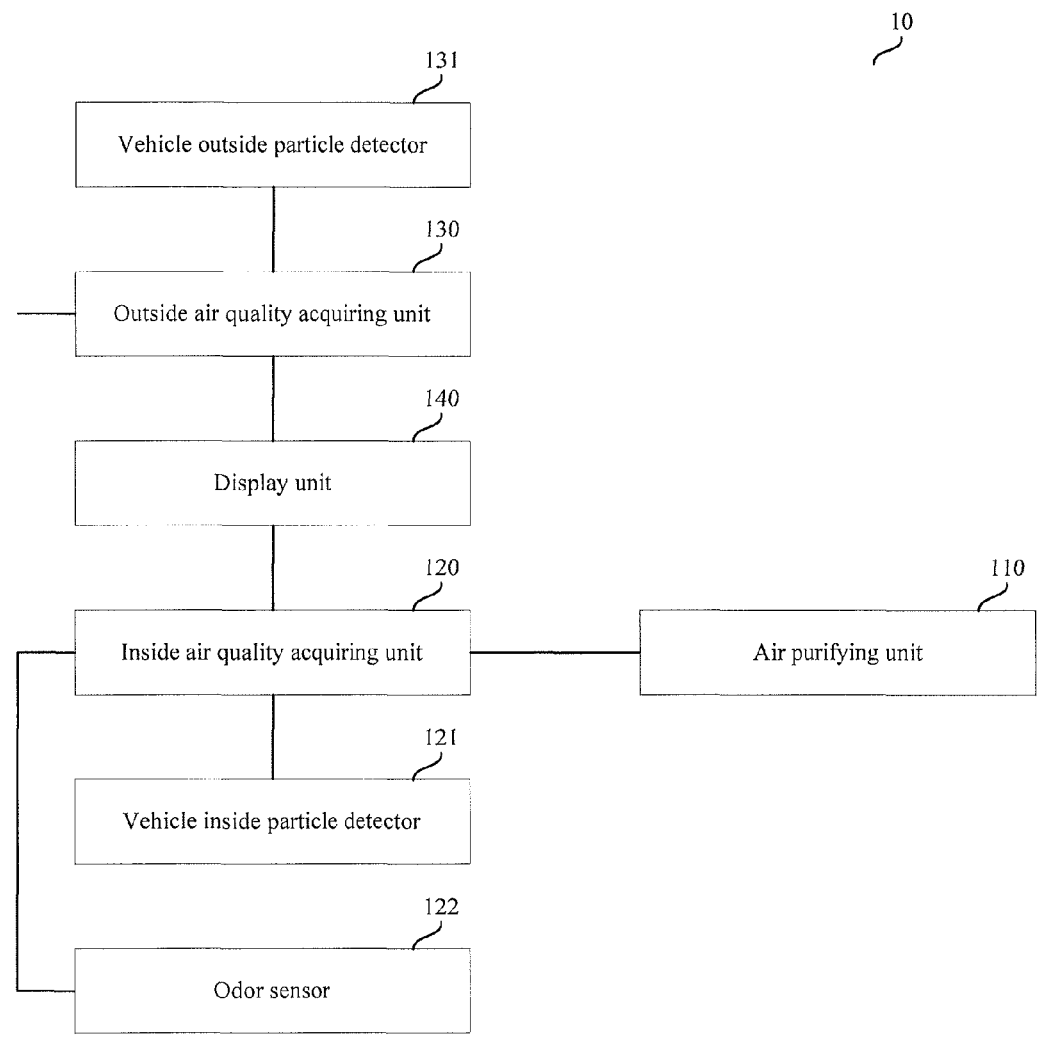
FIG. 1 is a block diagram showing a vehicle air conditioner device according to the first embodiment of the present invention.

FIG. 1 is a block diagram showing a vehicle air conditioner device 10 according to the first embodiment of the present invention. The vehicle air conditioner device 10 comprises an air purifying unit 110, an inside air quality acquiring unit 120, an outside air quality acquiring unit 130 and a display unit 140. The inside air quality acquiring unit 120 comprises a vehicle inside particle sensor 121 and an odor sensor 122, while the outside air quality acquiring unit 130 comprises a vehicle outside particle sensor 131.

The air purifying unit 110 is configured to purify the air inside the vehicle or the extracted external fresh air. For example, the over-standard air inside the vehicle or the external fresh air can be extracted into the purifying unit, and then a relatively clean and healthy air is discharged to the inside of the vehicle by purifying. The air purifying unit 110 is, for example, a filter with activated carbon.

The vehicle outside particle sensor 131 is disposed outside the vehicle and is configured to detect the content of specific particles, such as PM 2.5 (inhalable particles with diameters smaller than 2.5 micrometers) or Total Suspended Particulate, in the ambient air (air outside the vehicle), and send the detection result of the particle content to the outside air quality acquiring unit 130. Then, the outside air quality acquiring unit 130 compares the detected particle content in the ambient air with grading standard values so as to obtain the air quality of the ambient air. The grading standard values usually have been built into the outside air quality acquiring unit 130 at the beginning of the vehicle leaving factory, and the data source thereof may either be the air quality grading standard data published by the country where the vehicle is sold or by the relevant international organization, or the standard data voluntarily set by the vehicle manufacturer based on actual needs, as long as it can objectively distinguish the good air quality from the bad air quality. Moreover, the outside air quality acquiring unit 130 can also receives the air quality of the area where the vehicle locates from the outside world in a wireless communication manner such as GPRS, 3G network or WLAN.

The vehicle inside particle sensor 121 is disposed inside the vehicle and is configured to detect the content of specific particles in the air inside the vehicle and send the detection result to the inside air quality acquiring unit 120. The odor sensor 122 is disposed inside the vehicle and is configured to detect odor in the air inside the vehicle and send the detection result to the inside air quality acquiring unit 120. The inside air quality acquiring unit 120 evaluates the air quality inside the vehicle based on the detected particle content and/or odor so as to obtain the air quality inside the vehicle. Similarly, the air quality evaluation standard may either be the evaluation standard published by the relevant country or organization, or the evaluation standard voluntarily set by the vehicle manufacturer based on actual needs. For example, the air quality inside and outside the vehicle can be divided into six levels, that is, excellent, good, slight, light, moderate and heavy. Of course, the division of the air quality into levels is not limited to the above-mentioned manner. For example, the air quality levels can be directly set as "Level 1, Level 2, Level 3 . . . ."

The inside air quality acquiring unit 120 and the outside air quality acquiring unit 130 respectively send the display data of the air quality inside and outside the vehicle to the display unit 140 so that the user inside the vehicle can view the display data. The display unit 140 may be, for example, a liquid crystal display. In the display unit 140, different air quality levels are displayed through different colors, and the current air quality level is instructed to the user. Moreover, other display methods can also be adopted. For example, only the current air quality level inside and outside the vehicle is displayed in the display area of the display unit 140, or the particle content outside the vehicle as well as the odor information and/or particle content insider the vehicle is directly displayed in the display area.

Further, the air conditioner device 10 can also comprise an internal circulation unit and an external circulation unit (not shown) respectively used for an internal circulation mode and an external circulation mode. The switching between the internal circulation mode and the external circulation mode is performed according to the air quality inside and outside the vehicle. In the external circulation mode, a fresh air extractor (not shown) disposed in a water tank transports the fresh air to the air conditioner device 10, and then the air purifying unit 110 performs purification processing such as filtering and heats the purified fresh air by means of an evaporator (not shown). In the internal circulation mode, the air is extracted from the space inside the vehicle into the air conditioner device 10, and is then purified and heated therein.

In addition, the air conditioner device 10 can also comprise a in-vehicle climate control unit for regulating the temperature, humidity, air volume and air supply mode, etc. inside the vehicle so as to acquire a comfortable in-vehicle environment. At this time, the display unit 140 can also display information such as the temperature, humidity and air speed inside the vehicle.

In the first embodiment, the air conditioner device 10 displays the air quality inside and outside the vehicle via the display unit 140. Therefore, the user can visually obtain the air quality inside and outside the vehicle, which meets the user's psychological need better as compared with the subjective feeling of the user.

Second Embodiment

Figure 2:
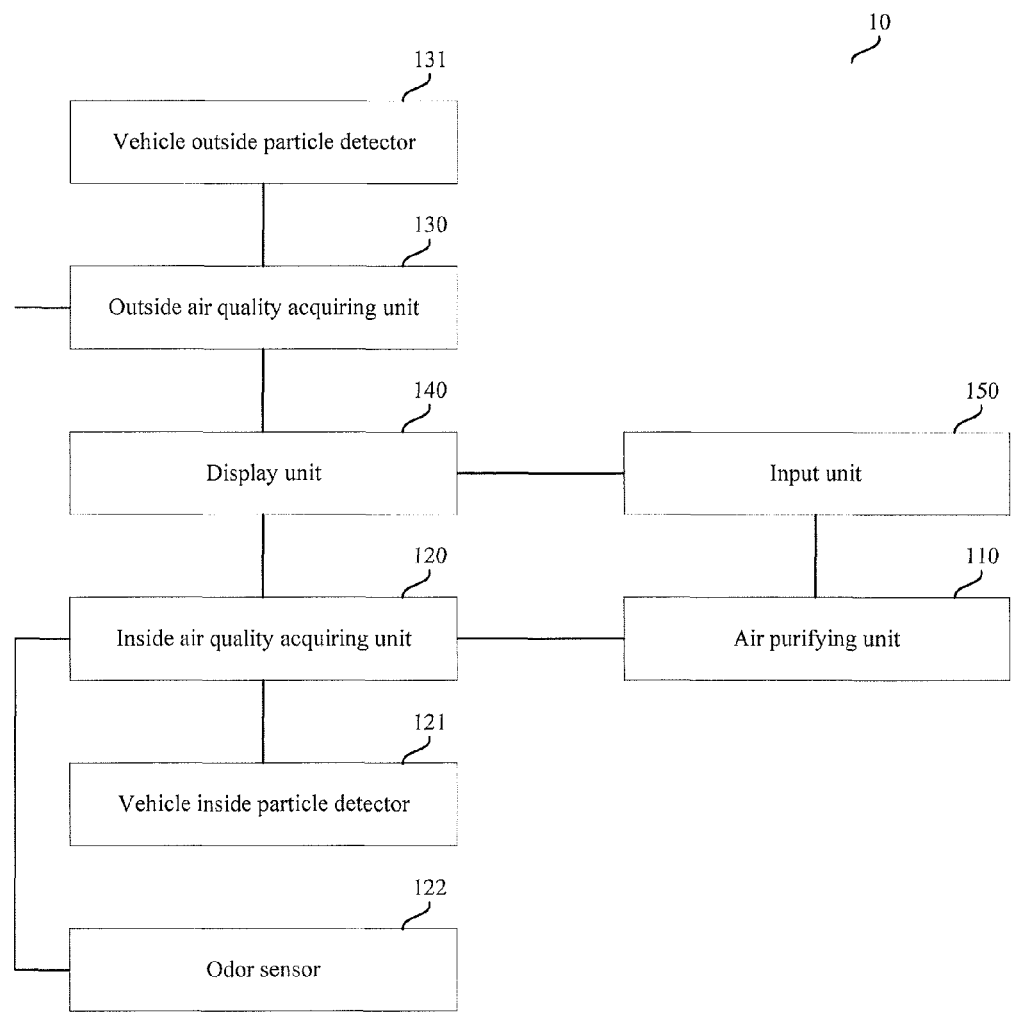
FIG. 2 is a block diagram showing a vehicle air conditioner device according to the second embodiment of the present invention.

FIG. 2 is a block diagram showing a vehicle air conditioner device according to the second embodiment of the present invention. The second embodiment differs from the first embodiment in that the second embodiment also comprises an input unit 150. The other content of the second embodiment is the same as the first embodiment.

The input unit 150 is configured to input various instructions to control the operation of the air conditioner device 10. Since the user can obtain the air quality inside and outside the vehicle via the display unit 140, the user can regulate the air quality inside the vehicle based on the personal will and actual needs (e.g. opening the window of the vehicle). For example, by inputting various instructions in the input unit 150, the internal circulation mode and the external circulation mode are manually switched, and the air purifying unit 110 and the in-vehicle climate control unit are started up or shut off.

In this embodiment, since the input unit 150 is provided, not only the technical effect of the first embodiment can be achieved, the user's actual needs and personal will for the air quality inside the vehicle can be further satisfied.

Third Embodiment

Figure 3:
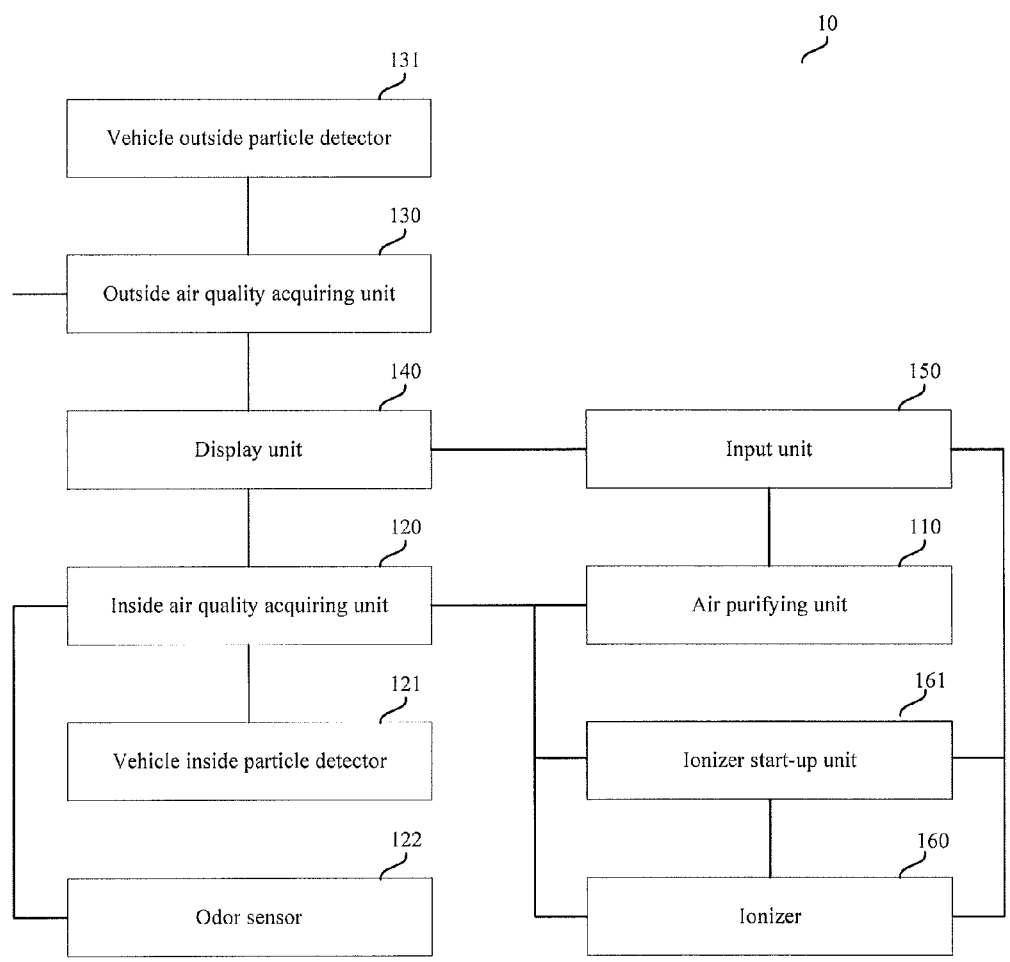
FIG. 3 is a block diagram showing a vehicle air conditioner device according to the third embodiment of the present invention.

FIG. 3 is a block diagram showing a vehicle air conditioner device according to the third embodiment of the present invention. The third embodiment differs from the second embodiment in that the air conditioner device 10 in the third embodiment also comprises an ionizer 160 and an ionizer start-up unit 161. The other content of the third embodiment is the same as the second embodiment.

The ionizer 160 is disposed inside the vehicle and is configured to generate a large amount of hydroxyl free radicals, oxygen free radicals and anions, etc. by partially ionizing the air flowing through the ionizer, and the generated free radicals promote the chemical process of bad smell removal and sterilization. Moreover, the generated anions can also be attached to suspended particles in the air, which makes the suspended particles fall down through self weight. Thereby, the suspended particles in the air are cleaned.

The ionizer start-up unit 161 is configured to start up the ionizer 160 when the running of the air purifying unit 110 cannot acquire a desired air quality. Moreover, since the user can obtain the air quality inside and outside the vehicle via the display unit 140, the user can start up or shut off the ionizer 160 via the input unit 150 based on actual needs or personal will.

In this embodiment, since the ionizer is used to assist the air purifying unit to purify the air, the further air purifying effect can be achieved, and the further user's demands for the air quality inside the vehicle can be satisfied.

Fourth Embodiment

Figure 4:
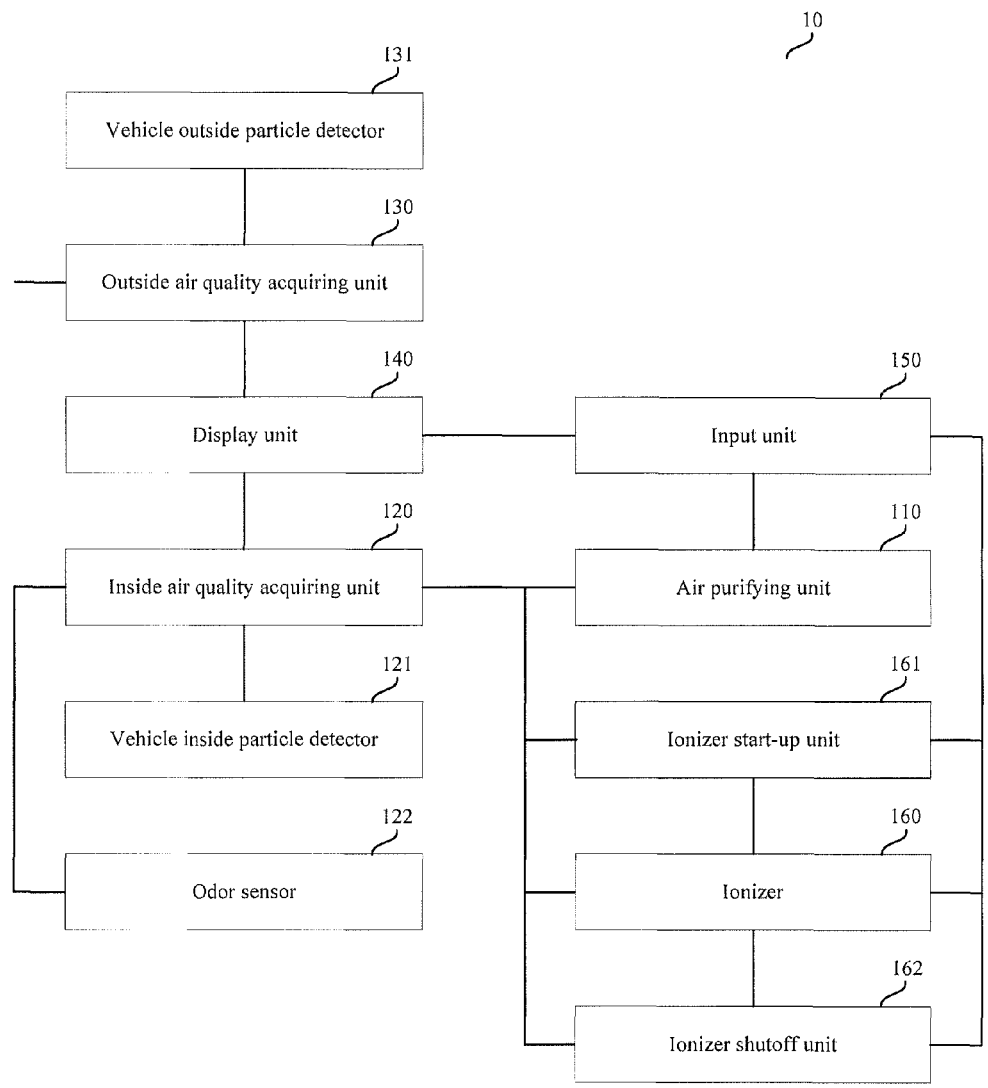
FIG. 4 is a block diagram showing a vehicle air conditioner device according to the fourth embodiment of the present invention.

FIG. 4 is a block diagram showing a vehicle air conditioner device according to the fourth embodiment of the present invention. The fourth embodiment differs from the third embodiment in that the fourth embodiment also comprises an ionizer shutoff unit 162. The other content of the fourth embodiment is the same as the third embodiment.

The ionizer shutoff unit 162 is configured to shut off the ionizer 160 after the air quality inside the vehicle has reached the desired air quality for a predetermined time period. Accordingly, this embodiment can automatically control the operation of the ionizer by using the ionizer start-up unit 161 and the ionizer shut-off unit 162. Moreover, the user can also manually control the ionizer 160. For example, the ionizer start-up unit 161 and the ionizer shutoff unit 162 can be shut off via the input unit 150. At this time, it is only possible to control the starting up and shutting off of the ionizer 160 via the input unit 150.

In addition, although the above-mentioned embodiments evaluate the air quality by using odor and particle content, the present invention is not limited to this. For example, a harmful gas sensor can be provided inside or outside the vehicle to acquire a more comprehensive air quality evaluation by detecting harmful gas.

The above are merely preferred embodiments of the present invention, which are used to describe the present invention rather than limit the present invention. For the one skilled in the art, any modification, equivalent replacement, improvement or the like within the spirit and principle of the present invention should be included in the protection scope of the present invention.

What is claimed is:

1. A vehicle air conditioner device, comprising:
   an air purifying unit for regulating air quality inside the vehicle;
   an inside air quality acquiring unit for acquiring air quality inside the vehicle;
   an outside air quality acquiring unit for acquiring air quality outside the vehicle; and
   a display unit for simultaneously displaying, in a way of intuitively providing to a user of the vehicle, information related to the acquired air quality inside the vehicle and information related to the acquired air quality outside the vehicle.

2. The vehicle air conditioner device according to claim 1, further comprising an odor sensor for detecting odor inside the vehicle, wherein
   the inside air quality acquiring unit evaluates the air quality inside the vehicle based on the odor inside the vehicle, and
   the display unit displays information related to the detected odor inside the vehicle.

3. The vehicle air conditioner device according to claim 1, further comprising a vehicle inside particle detector for detecting a particle content inside the vehicle, wherein
   the inside air quality acquiring unit evaluates the air quality inside the vehicle based on the particle content inside the vehicle, and
   the display unit displays information related to the detected particle content inside the vehicle.

4. The vehicle air conditioner device according to claim 1, further comprising a vehicle outside particle detector for detecting a particle content outside the vehicle, wherein
   the outside air quality acquiring unit evaluates the air quality outside the vehicle based on the particle content outside the vehicle, and
   the display unit displays information related to the detected particle content outside the vehicle.

5. The vehicle air conditioner device according to claim 1, wherein the outside air quality acquiring unit acquires the air quality outside the vehicle by communicating with the outside world.

6. The vehicle air conditioner device according to claim 5, wherein the outside air quality acquiring unit communicates with the outside world via a wireless network.

7. The vehicle air conditioner device according to claim 1, further comprising:
   an ionizer for purifying air inside the vehicle by partially ionizing the air flowing through the ionizer; and
   an ionizer start-up unit for starting up the ionizer when the running of the air purifying unit cannot acquire a desired air quality.

8. The vehicle air conditioner device according to claim 7, further comprising an ionizer shutoff unit for shutting off the ionizer after the air quality inside the vehicle has reached the desired air quality for a predetermined time period.

9. The vehicle air conditioner device according to claim 1, wherein the display unit displays, in the form of a graph, the information related to the air quality inside the vehicle and the information related to the air quality outside the vehicle in contrast to each other.

10. The vehicle air conditioner device according to claim 1, further comprising a fresh air extractor for transporting fresh air to the air purifying unit.

11. The vehicle air conditioner device according to claim 10, wherein the fresh air extractor is provided in a water tank of the vehicle.

12. A motor vehicle, comprising:
    a chassis; and
    a vehicle air conditioner device, the vehicle air conditioner device including:
       an air purifying unit for regulating air quality inside the vehicle;
       an inside air quality acquiring unit for acquiring air quality inside the vehicle;
       an outside air quality acquiring unit for acquiring air quality outside the vehicle; and
       a display unit for simultaneously displaying, in a way of intuitively providing to a user of the vehicle, information related to the acquired air quality inside the vehicle and information related to the acquired air quality outside the vehicle.

* * * * *